United States Patent [19]
Lukas-Laskey et al.

[11] Patent Number: 5,902,821
[45] Date of Patent: May 11, 1999

[54] USE OF CARBAZOLE COMPOUNDS FOR THE TREATMENT OF CONGESTIVE HEART FAILURE

[75] Inventors: Mary Ann Lukas-Laskey, Rosemont; Robert Ruffolo, Jr., Spring City; Neil Shusterman, Wynnewood, all of Pa.; Gisbert Sponer, Laudenbach; Klaus Strein, Hemsbach, both of Germany

[73] Assignee: Boehringer Mannheim Pharmaceuticals Corporation Smith Kline Corporation Limited Partnership No. 1, Gaithersburg, Md.

[21] Appl. No.: 08/875,603

[22] PCT Filed: Feb. 7, 1996

[86] PCT No.: PCT/EP96/00498

§ 371 Date: Dec. 29, 1997

§ 102(e) Date: Dec. 29, 1997

[87] PCT Pub. No.: WO96/24348

PCT Pub. Date: Aug. 15, 1996

[30] Foreign Application Priority Data

Feb. 8, 1995 [DE] Germany .......................... 195 03 995

[51] Int. Cl.⁶ .................................................. A61K 31/40
[52] U.S. Cl. ............................................................ 514/411
[58] Field of Search ................................................ 514/411

[56] References Cited

U.S. PATENT DOCUMENTS

| | | | |
|---|---|---|---|
| 4,888,179 | 12/1989 | Appelgren et al. ...................... | 424/480 |
| 5,308,862 | 5/1994 | Ohlstein .................................. | 514/411 |
| 5,312,828 | 5/1994 | Finkelstein et al. .................... | 514/381 |

OTHER PUBLICATIONS

J. of Cardiovascular Pharm; Senior, et al., "Effects of Carvedilol on Ventricular Arrhythmias", 1992, vol. 19, (Supp. 1): pp. S117–S121.
J. of Cardiovascuclar Pharm; DasGupta, et al., "The Effects of Intravenous Carvedilol, A New Multiple Action Vasodilatory β–Blocker, in Congestive Heart Failure", 1991, vol. 18, (Suppl. 1): pp. S12–S16.
American J. of Cardiology; DasGupta, et al., "Value of Carvedilol in Congestive Heart Failure Secondary to Coronary Artery Disease", 1990, vol. 66, pp. 1118–1123.
Z. Kardiol; A. Buchwald, et al., "Acute Hemodynamic Effects of the Beta–blocker Carvedilol in Heart Failure", 1990, vol. 79, No. 6, pp. 424–428.
JACC; DiLenarda, et al., "Acute Hemodynamic Effects of Carvedilol Versus Metroprolol In Idiopathic Dilated Cardiomyopathy", 1991, vol. 17, No. 2, Abstract 142A.
Frontiers in CHF; D. Tepper, "Multicenter Oral Carvedilol Heart Failure Assessment", 1996, vol. 2, No. 1, pp. 39–40.
J. of Cardiovascular Pharm; DasGupta, et al., 1992, vol. 19, (Suppl. 1): pp. S62–S67.
J. of Hypertension; C. Rosendorff, "Beta–blocking agents with vasodilator activity", 1993, vol. 11, (Suppl. 4): pp. S37–S40.
Cardiology; J. Lessem, et al., "Development of a Multi-action Beta–blocker", 1993, vol. 82, (Suppl. 3): pp. 50–58.
Drug Safety; W.J. Louis, et al., "A Risk–Benefit Assessment of Carvedilol in the Treatment of Cardiovascular Disorders", 1994, vol. 11, No. 2, pp. 86–93.
1994 American Heart Association, Inc., "A Randomized Trial of β–Blockade in Heart Failure", Circulation 90(4), Oct. 1994, pp. 1765–1773.
Waagstein et al., The Lancet, vol. 342, Dec. 11, 1993, "Beneficial effects of metroprolol in idiopathic dilated cardiomyopathy", pp. 1441–1446.
Ruffolo et al., Cardiology 1993; 82(suppl 3):24–28, "Cardioprotective Potential of Carvedilol", pp. 24–28.
Feuerstein et al., Journal of Hypertension 1993, vol. 11(suppl 4)., "Myocardial protection by the novel vasodilating beta–blocker, carvedilol; potential relevance of anti––oxidant activity".
Feuerstein et al., Journal of Cardiovascular Pharmacology, 19(suppl. 1) S138–141, "Myocardial Protection with Carvedilol"(1992).
DiBianco et al., The New England Journal of Medicine, vol. 320, Mar. 16, 1989, No. 11, "A comparison of oral milrinone, digoxin, and their combination in the treatment of patients . . . ", pp. 677–678.
Cohn et al., The New England Journal of Medicine, vol. 313, No. 24, "Effect of vasodilator therapy on mortality in chronic congestive heart failure", Jun., 1986, pp. 1547–1552.
McTavish et al., Drugs, 45(2): 232–258, 1993, "Carvedilol, A review of its pharmacodynamic and pharmacokinetic properties, and therapeutic efficacy".
Drugs; McTavish, et al., "Carvedilol—A Review of its Pharmacodynamic and Pharmacokinetic Properties, and Therepeutic Efficacy", 1993, vol. 45, No. 2, pp. 232–258.
Circulation; H. Krum, et al., "Effects of Carvedilol, a Vasodilator–β–Blocker, in Patients with Congestive Heart Failure Due to Ischemic Heart Disease", 1995, vol. 92, No. 2, pp. 212–218.
CBS–TV; CBS Evening News, Transcript, Jan. 27, 1993, 6:30–7:00pm.
CNBC; Steals and Deals, Transcript, Jan. 29, 1993, 8:30pm.
Circulation; DasGupta, et al., 1989, vol. 80, No. 4, (Suppl. II): pp. 116–117.
Drugs of Today; Ruffolo, et al., "Carvedilol (Kredex): A Novel Multiple Action Cardiovascular Agent", 1991, vol. 27, No. 7, pp. 465–492.

*Primary Examiner*—Phyllis G. Spivack
*Attorney, Agent, or Firm*—Nikaido, Marmelstein, Murray & Oram LLP

[57] ABSTRACT

A method of treatment using carvedilol is disclosed, wherein the carvedilol decreases the mortality caused by congestive heart failure in patients. The patients are titrated with low amounts of carvedilol, with the initial titration dosage being only 10 to 30% of the daily maintenance dose.

11 Claims, No Drawings

USE OF CARBAZOLE COMPOUNDS FOR THE TREATMENT OF CONGESTIVE HEART FAILURE

This application is a 371 of PCT/EP96/00498 filed Feb. 7, 1996.

FIELD OF THE INVENTION

The present invention relates to a new method of treatment using compounds which are dual non-selective β-adrenoceptor and $\alpha_1$-adrenoceptor antagonists in particular the carbazolyl-(4)-oxypropanolamine compounds of Formula I, preferably carvedilol, for decreasing the mortality of patients suffering from congestive heart failure (CHF). The invention also relates to a method of treatment using compounds which are dual non-selective β-adrenoceptor and $\alpha_1$-adrenoceptor antagonists, in particular the carbazolyl-(4)-oxypropanolamine compounds of Formula I, preferably carvedilol, in conjunction with one or more other therapeutic agents, said agents being selected from the group consisting of angiotensin converting enzyme (ACE) inhibitors, diuretics, and cardiac glycosides, for decreasing the mortality of patients suffering from CHF. The invention further relates to an incremental application scheme for administering compounds which are β-adrenoreceptor and $\alpha_1$-adrenoreceptor antagonists.

BACKGROUND OF THE INVENTION

Congestive heart failure occurs as a result of impaired pumping capability of the heart and is associated with abnormal retention of water and sodium. Traditionally, treatment of chronic mild failure has included limitation of physical activity, restriction of salt intake, and the use of a diuretic. If these measures are not sufficient, a cardiac glycoside, which is an agent that increases the force of mycardial contraction, is typically added to the treatment regimen.

Subsequently, angiotensin converting enzyme inhibitors, which are compounds that prevent the conversion of angiotensin I into the pressor-active angiotensin II, are prescribed for chronic treatment of congestive heart failure, in conjunction with a diuretic, a cardiac glycoside, or both.

Also, congestive heart failure is a well-known cardiac disorder which results in an excess mortality. Applefeld, M. M., (1986) Am. J. Med. 80, Suppl. 2B, 73–77. Therefore, therapeutic agents that would decrease the mortality resulting from CHF in patients suffering therefrom are highly desirable.

SUMMARY OF THE INVENTION

The present invention provides a new use of compounds which are dual non-selective β-adrenoceptor and $\alpha_1$-adrenoceptor antagonists for the preparation of medicaments for the treatment of congestive heart failure. In particular, the carbazolyl-(4)-oxypropanolamine compounds of Formula I are preferred, alone or in conjunction with one or more other therapeutic agents, said agents being selected from the group consisting of ACE inhibitors, diuretics, and cardiac glycosides, as therapeutics for decreasing mortality resulting from congestive heart failure in mammals. In particular, the present invention preferably provides a method of treatment, alone or in conjunction with one or more other therapeutic agents, said agents being selected from the group consisting of ACE inhibitors, diuretics, and cardiac glycosides, for the compound of Formula I wherein $R_1$ is —H, $R_2$ is —H, $R_3$ is —H, $R_4$ is —H, X is O, Ar is phenyl, $R_5$ is ortho —OCH$_3$, and $R_6$ is —H, said compound being better known as carvedilol, which is (1-(carbazol-4-yloxy-3-[[2-(2-methoxyphenoxy) ethyl]amino]2-propanol), or a pharmaceutically acceptable salt thereof.

DETAILED DESCRIPTION OF THE INVENTION

U.S. Pat. No. 4,503,067 discloses carbazolyl-(4)-oxypropanolamine compounds of Formula I:

TABLE 1

US Carvedilol Heart Failure Trials-Baseline Characteristics

| Characteristic | Placebo (n ≈ 356) | Carvedilol (n = 624) |
|---|---|---|
| Age, mean + SD (years) | 59.9 + 11.7 | 58.8 − 11.8 |
| Sex (% men) | 62% | 62% |
| Etiology (% ischemic) | 43% | 40% |
| Severity of CHF | | |
| Class II | 41% | 41% |
| Class III–IV | 40% | 39% |
| Unknown | 19% | 20% |
| LV ejection fraction, mean + SD | 0.22 + 0.07 | 0.23 − 0.08 |
| 6 Minute walk (m + SD) | 373 + 88 | 379 + 81 |
| Blood pressure (mmHg) | 115/73 | 115/73 |
| Heart rate (bpm + SD) | 85 ± 13 | 86 ± 13 | wherein $R_1$ is hydrogen, lower alkanoyl of up to 6 carbon atoms or aroyl selected from benzoyl, and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms, $R_4$ is hydrogen or lower alkyl of up to 6 carbon atoms, or when X is oxygen, $R_4$ together with $R_5$ can represent —CH$_2$—O—;

X is a valency bond, —CH$_2$, oxygen or sulfur;

Ar is selected from phenyl naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —CONH$_2$— group, lower alkoxy of up to 6 carbon atoms, benzyloxy, lower alkylthio of up to 6 carbon atoms, lower alkysulphonyl of up to 6 carbon atoms and lower alkylsulphonyl of up to 6 carbon atoms; or $R_5$ and $R_6$ together represent methylenedioxy; and pharmaceutically acceptable salts thereof.

This patent further discloses a compound of Formula I, better known as carvedilol, which is (1-(carbazol-4-yloxy-3-[[2-(2-methoxyphenoxy)ethyl]amino](2-propanol), having the structure shown in Formula II

TABLE 2

Evaluation of Mortality in US Carvedilol CHF Studies

| | Carvedilol | Placebo | Risk reduction (95% Cl) | p value* |
|---|---|---|---|---|
| All Cause Mortality | 18/624 (2.9%) | 29/356 (8.2%) | 67% (42–81) | <0.001 |
| Class II CHF | 7/361 (1.9%) | 12/202 (5.9%) | 68% (20–97) | 0.015 |

TABLE 2-continued

Evaluation of Mortality in US Carvedilol CHF Studies

|  | Carvedilol | Placebo | Risk reduction (95% CI) | p value* |
|---|---|---|---|---|
| Class III–IV CHF | 11/263 (4.2%) | 17/154 (11.0%) | 66% (30–84) | 0.004 |
| Ischemic Etiology | 10/311 (3.2%) | 16/178 (8.9%) | 67% (32–85) | 0.003 |
| Non-Ischemic Etiology | 8/313 (2.5%) | 13/178 (7.3%) | 67% (20–86) | 0.014 |

*Cochran-Mantel-Haensel Antaysis

Formula I compounds, of which carvedilol is exemplary, are novel multiple action drugs useful in the treatment of mild to moderate hypertension. Carvedilol is known to be both a competitive non-selective β-adrenoceptor antagonist and a vasodilator, and is also a calcium channel antagonist at higher concentrations. The vasodilatory actions of carvedilol result primarily from $α_1$-adrenoceptor blockade, whereas the β-adrenoceptor blocking activity of the drug prevents reflex tachycardia when used in the treatment of hypertension. These multiple actions of carvedilol are responsible for the antihypertensive efficacy of the drug in animals, particularly in humans. See Willette, R. N., Sauermelch, C. F. & Ruffolo, R. R., Jr. (1990) Eur. J. Pharmacol., 176, 237–240; Nichols, A. J., Gellai, M. & Ruffolo, R. R. Jr. (1991) Fundam. Clin. Pharmacol., 5, 25–38; Ruffolo, R. R., Ir., Gellai, M., Hieble, J. P., Willette, R. N. & Nichols, A. J. (1990) Eur. J. Clin. Pharmacol., 38, S82–588, Ruffolo, R. R., Ir., Boyle, D. A., Venuti, R. P, & Lukas, M. A. (1991) Drugs of Today, 27, 465–492: and Yue, T.-L., Cheng, H., Lysko, P. G., Mckenna, P. J., Feuerstein, R., Gu, I., Lysko, K. A., Davis, L. L. & Feuerstein, G. (1992) J. Pharmacol Exp. Ther., 263, 92–98.

The antihypertensive action of carvedilol is mediated primarily by decreasing total peripheral vascular resistance without causing the concomitant reflex changes in heart rate commonly associated with other antihypertensive agents. Willette, R. N., et al. supra; Nichols, A. J., et al. supra. Ruffolo, R. R., Jr., Gellai, M., Hieble, J. P. Willette, R. N. & Nichols, A. I. (1990) Eur. J. Clin. Pharmacol., 38, S82–S88. Carvedilol also markedly reduces infarct size in rat, canine and porcine models of acute myocardial infarction, Ruffolo, R. R., Jr., et al., Drugs of Today, supra, possibly as a consequence of its antioxidant action in attenuating oxygen free radical-initiated lipid peroxidation, Yue, T. L., et al. supra.

Recently, it has been discovered in clinical studies that pharmaceutical compounds which are dual non-selective β-adrenoceptor and $α_1$-adrenoceptor antagonists, in particular the compounds of Formula I, preferably carvedilol, alone or in conjunction with conventional agents, said agents being ACE inhibitors, diuretics, and cardiac glycosides, are effective therapeutic agents for treating CHF. The use of agents, such as carvedilol in treating CHF is surprising, since, in general, β-blockers are contraindicated in patients suffering from heart failure, because β-blockers are known to have undesirable cardiodepressive effects. The most surprising observation from the studies in which the instant compounds were used to treat CHF is that said compounds, in particular carvedilol, are able to decrease the mortality resulting from CHF in humans by about 67 percent. Furthermore, this result is present across all classifications of CHF and both etiologies (eschemic and non-eschemic). This result is surprising since two recent mortality studies using the β-blockers metoprolol (Waagstein, et al., (1993) Lancet, 342, 1441–1446) and bisoprolol (CIBIS investigators and committees, (1994) Circulation, 90, 1765–1773) in the treatment of CHF showed no difference in mortality between drug-treated patients and placebo-treated patients.

According to the method of treatment of the present invention, the desirable therapeutic effect of the compounds of Formula I, particularly carvedilol, may be augmented by using any one of said compounds: or any pharmaceutically acceptable salt of said compounds, in conjunction with ACE inhibitors, diuretics, and cardiac glycosides, which are effective therapeutic agents for the treatment of CHF. In particular, the preferred ACE inhibitors of the present invention are selected from the group consisting of captopril, lisinopril, fosinopril and enalapril, or any pharmaceutically acceptable salts thereof and the preferred diuretics of the present invention are hydrochlorothiazide furosemide, or torasemide or any pharmaceutically acceptable salts thereof The preferred cardiac glycosides of the present invention are digoxin, β-methyldigoxin or digitoxin. The desireable therapeutic benefits of the compounds of Formula I, particularly carvedilol, are additive with those of such ACE inhibitors, or diuretics, or cardiac glycosides when administered in combination therewith. Captopril is commercially available from E. R. Squibb & Sons. Inc. Lisinopril, enalapril and hydrochlorothiazide are commercially available from Merck & Co. Furosemide is commercially available from Hoechst-Roussel Pharmaceuticals, Inc. Digoxin is commercially available from Burroughs Wellcome Co. and Boehringer Mannheim GmbH, Digitoxin, β-Methyldigoxin, fosinopril and torasemide are commercially available from Boehringer Mannheim GmbH.

Compounds of Formula I may be conveniently prepared as described in U.S. Pat. No. 4,503,067. Carvedilol is commercially available from SmithKline Beecham Corporation and Boehringer Mannheim GmbH (Germany).

Pharmaceutical compositions of the compounds of Formula I, including carvedilol, alone or in combination with ACE inhibitors, or diuretics, or cardiac glycosides may be administered to patients according to the present invention in any medically acceptable manner, preferably orally. For parenteral administration, the pharmaceutical composition will be in the form of a sterile injectable liquid stored in a suitable container such as an ampoule, or in the form of an aqueous or nonaqueous liquid suspension. The nature and composition of the pharmaceutical carrier, diluent or excipient will, of course, depend on the intended route of administration, for example whether by intravenous or intramuscular injection.

Pharmaceutical compositions of the compounds of Formula I for use according to the present invention may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as ethanol, polyvinylpyrrolidone, gelatin, hydroxy cellulose, acacia, polyethylene glycol, mannitol, sodium chloride or sodium citrate.

Alternatively, these compounds may be encapsulated, tableted or prepared in a emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, ethanol, and water. Solid carriers include starch, lactose, calcium sulfate dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms: or milling, mixing and filling for hard gelatin capsule forms. When a liquid carrier is used, the preparation will be in the form of a syrup, elixir, emulsion or an aqueous or non-aqueous suspension.

Such a liquid formulation may be administered directly p.o. or filled into a soft gelatin capsule.

Compounds having the above-mentioned dual properties are preferably administered following a three-stage application scheme. This scheme is characterized by the fact that incremental dosages of the active ingredient are administered to patients over a certain period of time, until the regular maintenance dosage is received. If this maintenance dosage is defined as the setting value being 100%, it was found that the application regimen in a first phase should extend for a period of 7–28 days, whereby only 10–30% of the setting dose are administered. Following this phase, a second application regimen should follow, wherein a dosage of 20–70% of the setting dose is administered to the patient for a period of 7–28 days. After termination of this phase, the third application period follows, wherein the daily complete setting dose (maintenance dose) is administered. The daily maintenance dose can vary between 10–100 mg of said active ingredient.

In case of carvedilol, dosing in humans for the treatment of disease according to the present invention should not exceed a dosage range of from about 3.125 to about 50 mg of the compounds of Formula I, particularly carvedilol, preferably given twice daily. As one of ordinary skill in the art will readily comprehend, the patient should be started on a low dosage regimen of the desired compound of Formula I, particularly carvedilol, and monitored for well-known symptoms of intolerance, e.g., fainting, to such compound. Once the patient is found to tolerate such compound, the patient should be brought slowly and incrementally up to the maintenance dose. The preferred course of treatment is to start the patient on a dosage regimen with formulations which contain either 3.125 or 6.25 mg of active compound per single unit, preferably given twice daily, for 7–28 days. The choice of initial dosage most appropriate for the particular patient is determined by the practitioner using well-known medical principles, including, but not limited to, body weight. In the event that the patient exhibits medically acceptable tolerance of the compound for two weeks, the dosage is doubled at the end of the two weeks and the patient is maintained at the new, higher dosage for an additional period, preferably to two more weeks, and observed for signs of intolerance. This course is continued until the patient is brought to a maintenance dose. The preferred maintenance dose is 25.0 mg of active compound per single unit, preferably given twice daily, for patients having a body weight of up to 85 kg. For patients having a body weight of over 85 kg, the maintenance dose is between about 25.0 mg and about 50.0 mg, preferably given twice daily, preferably about 50.0 mg of active compound per single unit, preferably given twice daily.

The present invention relates also to method of treatment for decreasing mortality resulting from congestive heart failure in mammals comprising internally administering to said mammal in need thereof an effective amount of carvedilol according to the following schedule:

(a) a pharmaceutical formulation which contains either 3.125 or 6.25 mg carvedilol per single unit for a period of 7–28 days, given once or twice daily.

(b) thereafter a pharmaceutical formulation which contains 12.5 mg carvedilol per single unit for a period of additional 7–28 days, given once or twice daily and (c) finally a pharmaceutical formulation which contains either 25.0 or 50.0 mg carvedilol per single unit, given once or twice daily as a maintenance dose.

Dosing in humans for the treatment of disease according to the present invention includes the combination of compounds of Formula I with conventional agents. For example, the usual adult dosage of hydrochlorothiazide is 25–100 mg daily as a single dose or divided dose. The recommended starting dose for enalapril is 2.5 mg administered once or twice daily. The usual therapeutic dosing range for enalapril is 5–20 mg daily, given as a single dose or two divided doses. For most patients the usual initial daily dosage of captopril is 25 mg three times per day (tid), with most patients having a satisfactory clinical improvement at 50 or 100 mg three times per day (tid).

It will be appreciated that the actual preferred dosages of the compounds being used in the compositions of this invention will vary according to the particular composition formulated, the mode of administration, the particular site of administration and the host being treated.

No unacceptable toxicological effects are expected when the compounds of Formula I, including the compound of Formula II, are used according to the present invention. The example which follows is intended in no way to limit the scope of this invention, but is provided to illustrate how to use the compounds of this invention. Many other embodiments will be readily apparent to those skilled in the art.

EXPERIMENTAL

Mortality Studies in CHF Patients

Summary

To determine if β-adrenergic blockade might inhibit the deleterious effects of the sympathetic nervous system on survival in heart failure (CHF), 1052 patients with CHF were prospectively enrolled into a multicenter trial program, in which patients were randomly assigned (double-blind) to 6–12 months' treatment with placebo (PBO) or carvedilol (CRV). After a common screening period, patients with class II-IV CHF (see next paragraph for the definitions of the classification of CI) and an ejection fraction <0.35 were assigned to one of four protocols based on performance on a 6-minute walk test. PBO or CRV was added to existing therapy with digoxin, diuretics and an ACE inhibitor. All-cause mortality was monitored by a prospectively constituted Data and Safety Monitoring Board (DSMB). After 25 months of enrollment, the DSMB recommended termination of the program because of a favorable effect of CRV on survival. By intention-to-eat, mortality was 8.2% in the PBO group but only 2.9% in the CRV group (P=0.0001. Cochran-Mantel-Haensel analysis). This represented a reduction in risk of death by CRV of 67% (95% CI: 42% to 81%). The treatment effect was similar in patients with class II and class III–IV symptoms. Mortality was reduced in class II patients from 5.9% to 1.9%, a 68% reduction (95% CI: 20% to 97%) [P=0.015,), and in class III–IV patients from 11.0% to 4.2%. a 67% reduction (95% CI 30% to 84%), [P=0.004, log-rank].

Importantly, the effect of CRV was similar in ischemic heart disease (risk reduced by 67%. P=0.003) and in nonischemic dilated cardiomyopathy (risk reduced by 67%. P=0.014). In conclusion, the addition of CRV to conventional therapy is associated with a substantial (67%) reduction in the mortality of patients with chronic CHF. The treatment effect is seen across a broad range of severity and etiology of disease.

As used herein, by "Class II CHF" is meant patients with cardiac disease resulting in slight or moderate limitation of physical activity. They are comfortable at rest. Ordinary physical activity results in fatigue, palpitations, dyspnea, or anginal pain. By "Class III CHF" is meant patients with cardiac disease resulting in marked limitations of physical activity. They are comfortable at rest. Less than ordinary physical activity results in fatigue, palpitations, dyspnea, or anginal pain. By "Class IV CI" is meant patients with cardiac disease resulting in inability to carry on any physical activity without discomfort. symptoms or cardiac insufficiency, or of the anginal syndrome. By "less than ordinary physical activity" is meant climbing, one flight of stairs, or walking two hundred yards.

Design of Study

Patients on background therapy with diuretics. ACE inhibitors and/or digoxin were stratified on the basis of baseline submaximal exercise performance, into one of four trials:

study 220, a dose response study in moderate (NYHA II–IV) CHF with exercise testing as a primary endpoint study 221, a dose titration study in moderate (NYHA II–IV) CI with exercise testing as a primary endpoint study 239, a dose titration study in severe (NYHA III–IV) CHF with quality of life as a primary endpoint study 240, a dose titration study in mild (NYHA II–III) CHF with progression of CHF as a primary endpoint Sixty-four centers in the US participated in the trial program. All sites conducted protocols 239 and 240, while 33 performed protocol 220 and 31 performed protocol 221.

Although each trial had its own individual objectives, the overall program objective defined prospectively was evaluation of all-cause mortality. Based upon a projected enrollment of 1100 patients, the program had 90% power to detect a 50% reduction in mortality (two-sided) between carvedilol and placebo, assuming a mortality rate in the placebo group of 12% over the duration of the trials ($\alpha$=0.05).

Randomization was preceded by a screening and challenge period common to the four protocols The purpose of the screening period was to quality patients for study entry obtain reproducible baseline measurements, and stratify patients into the appropriate trial based on submaximal exercise testing. During the challenge period, patients received low-dose open-label carvedilol (6.25 mg b.i.d.) for two weeks. Patients unable to tolerate this dose did not proceed to randomization. Patients tolerating low-dose carvedilol were then randomized to blinded medication (carvedilol or placebo) with the dose titrated over several weeks in the range of 6.25 to 50 mg b.i.d. (or equivalent level of placebo). The maintenance phase of each study ranged from six to 12 months, after which patients had the option of receiving open-label carvedilol in an extension study.

Results

The analysis presented below corresponds to the data set on which the DSMB made the recommendation to terminate the trials. Included in this intent-to-eat analysis are all patients enrolled in the US trials as of Jan. 20, 1995; 624 receiving carvedilol and 356 placebo. An analysis of baseline patient characteristics (Table 1) shows good balance between the randomized groups.

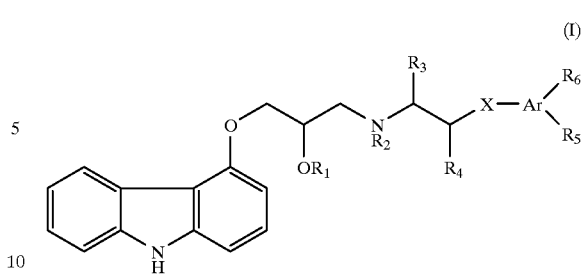

(I)

The overall mortality results for the program are shown in Table 2. All deaths that occurred during the intent-to-treat period are included. Treatment with carvedilol resulted in a 67% reduction in the risk of all-cause morality. Analysis of mortality by certain baseline characteristics shows this to be a broad effect regardless of severity or etiology of CI. The effect was uniform in patients with mild heart failure or moderate to severe heart failure. Similarly, the mortality reduction was equivalent in patients with ischemic or non-ischemic heart failure.

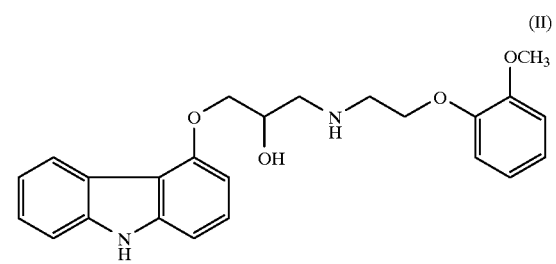

(II)

The foregoing is illustrative of the compounds of this invention. This invention, however, is not limited to the precise embodiment described herein, but encompasses all modification within the scope of the claims which follow.

We claim:

1. A method of decreasing mortality caused by congestive heart failure in a patient in need of such decrease, said method comprising:

administering to said patient first dosages at least daily for a period of from 7 to 28 days, said first dosages each comprising carvedilol, then administering to said patient second dosages at least daily for a period of from 7 to 28 days, said second dosages each containing carvedilol, and then administering to said patient third dosages daily for a maintenance period, said third dosages each comprising carvedilol, said third dosages each comprising a daily maintenance dose in the range of from about 10 mg to about 100 mg of carvedilol, said first dosages each comprising carvedilol in an amount which is 10–30% of said daily maintenance dose, said second dosages each comprising carvedilol in an amount which is 20–70% of said daily maintenance dose.

2. The method of claim 1, wherein the daily maintenance dose is about 25 mg or about 50 mg.

3. The method of claim 1, further comprising administering to said patient at least one other therapeutic agent selected from the group consisting of angiotensin converting enzyme inhibitors, diuretics and cardiac glycosides.

4. The method of claim 3, wherein the angiotensin converting enzyme inhibitor is selected from the group consisting of captopril, lisinopril, fosinopril, enalapril and pharmaceutically acceptable salts of captopril, lisinopril, fosinopril and enalapril.

5. The method of claim 3, wherein said diuretic is selected from the group consisting of hydrochlorothiazide, torasemide, furosemide, and pharmaceutically acceptable salts of hydrochlorothiazide, torasemide and furosemide.

6. The method of claim 3, wherein said cardiac glycoside is selected from the group consisting of digoxin, β-methyl-digoxin and digitoxin.

7. A method of decreasing mortality caused by congestive heart failure in a patient, said method comprising administering to said patient first dosages once or twice daily, for a period of from 7 to 28 days, said first dosages each comprising carvedilol in an amount of about 3.125 mg or 6.25 mg, then administering to said patient second dosages once or twice daily, for a period of from 7 to 28 days, said second dosages each comprising carvedilol in an amount of about 12.5 mg, and then administering to said patient maintenance third dosages once or twice daily, said third dosages each comprising carvedilol in an amount of about 25.0 mg or about 50.0 mg.

8. A method as recited in claim 7, wherein at least one of said first, second and maintenance dosages further comprises at least one other therapeutic agent selected from the group consisting of an angiotensin converting enzyme inhibitor, a diuretic and a cardiac glycoside.

9. A method of treating to decrease mortality resulting from congestive heart failure in a patient in need of such treatment, said method comprising administering to said patient carvedilol, alone or in combination with at least one other therapeutic agent, in unit dosages once or twice daily, for a period of from 7 to 28 days, said unit dosages each comprising a pharmaceutical formulation comprising carvedilol in an amount of about 3.125 mg or about 6.25 mg.

10. A method of treating congestive heart failure in a patient in need of such treatment, said method comprising:

administering to said patient first dosages at least daily for a period of from 7 to 28 days, said first dosages each comprising carvedilol, then administering to said patient second dosages at least daily for a period of from 7 to 28 days, said second dosages each comprising carvedilol, and then administering to said patient third dosages daily for a maintenance period, said third dosages each comprising carvedilol, said third dosages each comprising a daily maintenance dose in the range of from about 10 mg to about 100 mg of carvedilol, said first dosages each comprising carvedilol in an amount which his 10–30% of said daily maintenance dose, said second dosages each comprising carvedilol in an amount which is 20–70% of said daily maintenance dose.

11. Method of claim 10, wherein carvedilol is administered to the patient once or twice daily.

* * * * *